United States Patent
Imamura et al.

(10) Patent No.: US 8,442,286 B2
(45) Date of Patent: May 14, 2013

(54) IMAGE PROCESSING APPARATUS AND IMAGE PROCESSING METHOD FOR A TOMOGRAM OF AN EYE REGION

(75) Inventors: Hiroshi Imamura, Tokyo (JP); Yoshihiko Iwase, Yokohama (JP); Kiyohide Satoh, Kawasaki (JP); Akihiro Katayama, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 420 days.

(21) Appl. No.: 12/759,488

(22) Filed: Apr. 13, 2010

(65) Prior Publication Data

US 2010/0202677 A1 Aug. 12, 2010

Related U.S. Application Data

(63) Continuation of application No. PCT/JP2009/003675, filed on Aug. 3, 2009.

(30) Foreign Application Priority Data

Oct. 17, 2008 (JP) .................................. 2008-269186

(51) Int. Cl.
*G06K 9/00* (2006.01)
(52) U.S. Cl.
USPC ................................ 382/128; 128/922; 378/4
(58) Field of Classification Search .................. 382/100, 382/128, 129, 130, 131, 132; 128/922; 378/4–27; 600/318, 383, 356, 162, 236
See application file for complete search history.

(56) References Cited

U.S. PATENT DOCUMENTS

| | | | | |
|---|---|---|---|---|
| 7,203,351 | B1 * | 4/2007 | Swindale et al. | 382/128 |
| 7,593,559 | B2 * | 9/2009 | Toth et al. | 382/128 |
| 8,045,176 | B2 * | 10/2011 | Everett et al. | 356/497 |
| 8,118,752 | B2 * | 2/2012 | Hetling et al. | 600/558 |
| 2007/0103693 | A1 * | 5/2007 | Everett et al. | 356/479 |
| 2010/0278402 | A1 * | 11/2010 | Everett et al. | 382/128 |

FOREIGN PATENT DOCUMENTS

| | | |
|---|---|---|
| JP | 2007-275318 A | 10/2007 |
| JP | 2007-325831 A | 12/2007 |
| JP | 2008-073099 A | 4/2008 |
| JP | 2008-154704 A | 7/2008 |
| JP | 2008-206684 A | 9/2008 |
| JP | 2008-209166 A | 9/2008 |
| JP | 2009-061203 A | 3/2009 |

OTHER PUBLICATIONS

"Advance of Optical Coherence Tomography in Ophthalmology", The Journal of Japan Society for Laser Surgery and Medicine, JSLSM, vol. 28, No. 2, pp. 146-159 (2007, Japan).

(Continued)

*Primary Examiner* — Anand Bhatnagar
(74) *Attorney, Agent, or Firm* — Carter, DeLuca, Farrell & Schmidt LLP

(57) ABSTRACT

There is provided a technique for adaptively acquiring, from a tomogram of an eye region, diagnosis information data of the eye region which is used for the diagnosis of a plurality of kinds of diseases, without increasing load on a user. A layer acquisition unit (331) acquires a predetermined layer area from the tomogram of the eye region. A changing unit (332) changes an algorithm for the acquisition of diagnosis information data as information used for the diagnosis of the eye region from the tomogram based on the information data extracted from the layer area. A quantifying unit (336) acquires diagnosis information data from the tomogram based on the changed algorithm.

18 Claims, 12 Drawing Sheets

OTHER PUBLICATIONS

Japanese Office Action dated Jan. 20, 2012 for application No. 2011-177249.

Japanese Office Action dated Aug. 3, 2012, issued in corresponding Japanese application No. 2012-064433.

* cited by examiner

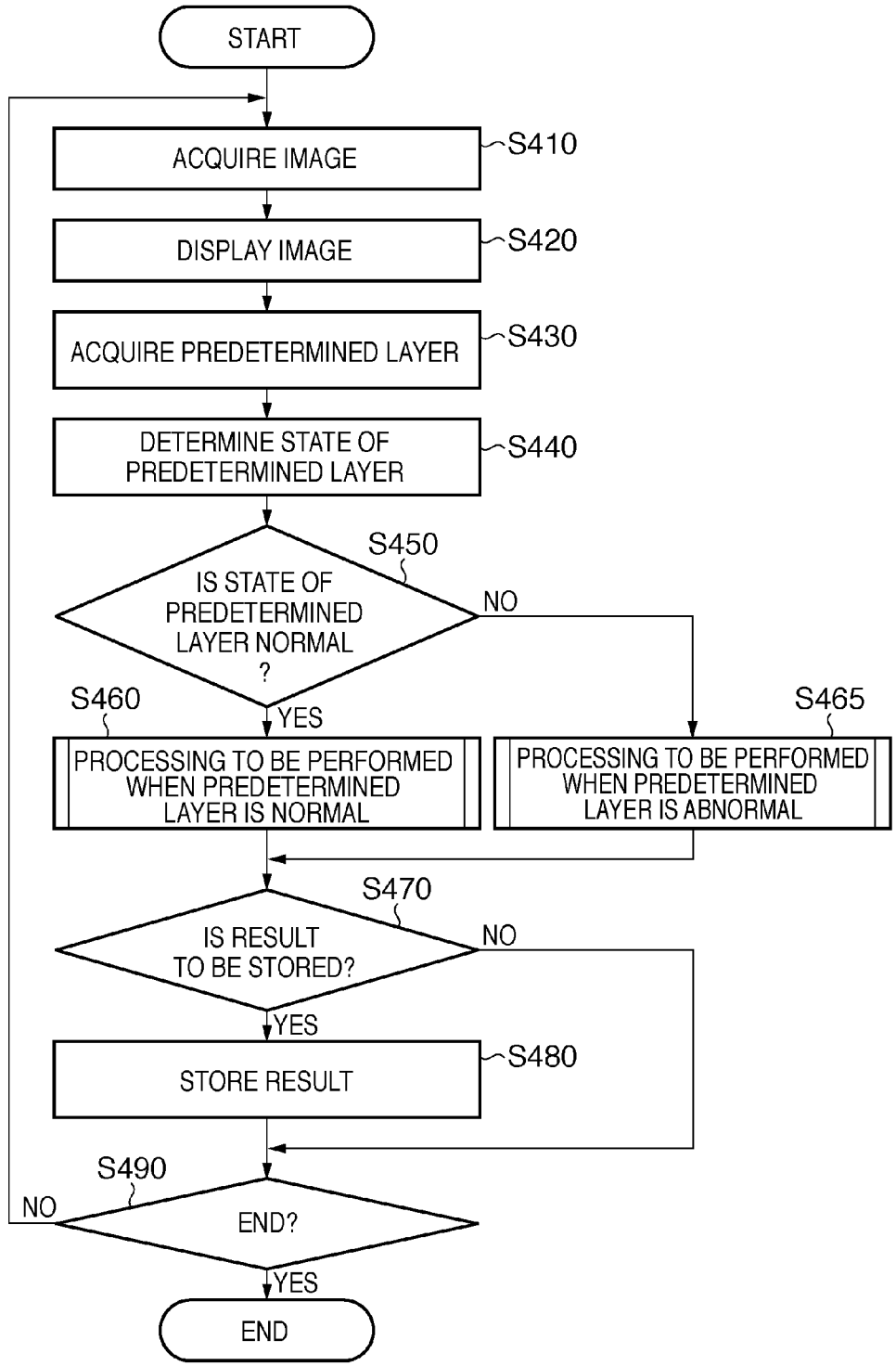

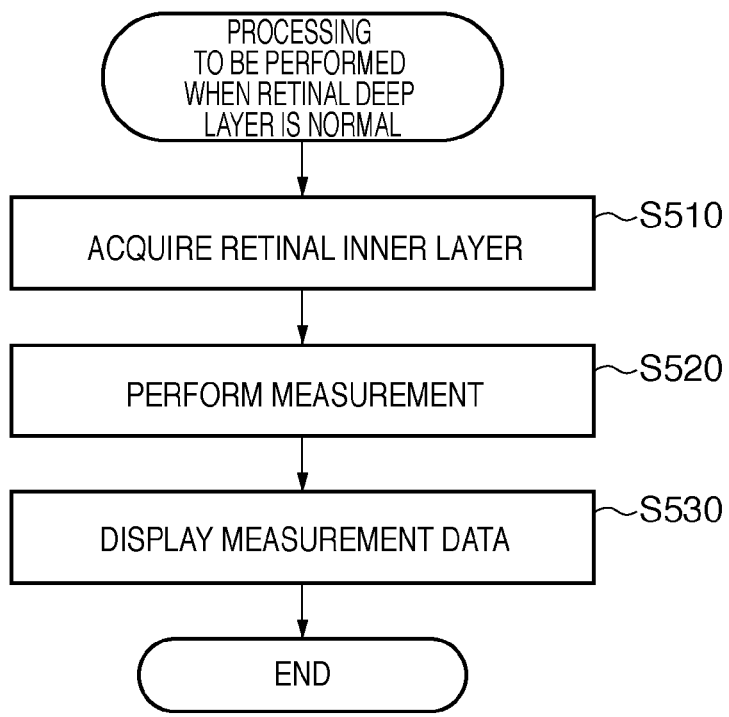
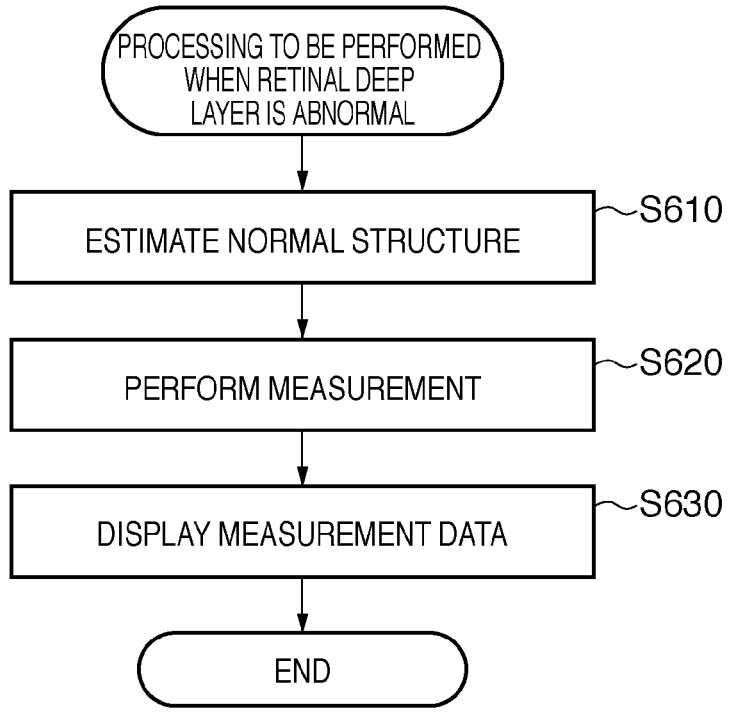

FIG. 7
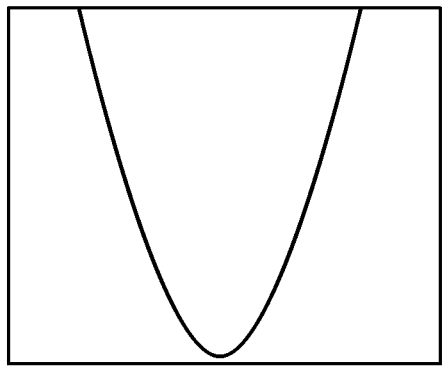
$\rho(x) = x^2$
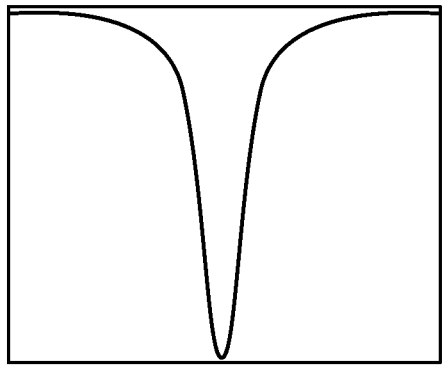
$\rho(x) = \dfrac{x^2}{\sigma + x^2}$
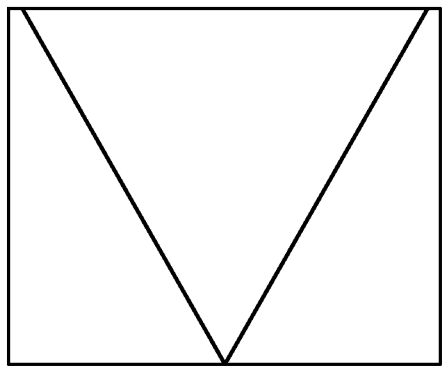
$\rho(x) = 2(\sqrt{1 + x^2/2} - 1)$

IMAGE PROCESSING APPARATUS AND IMAGE PROCESSING METHOD FOR A TOMOGRAM OF AN EYE REGION

CROSS REFERENCE

This application is a continuation of International Application No. PCT/JP2009/003675, filed Aug. 3, 2009, which claims the benefit of Japanese Patent Application No. 2008-269168, filed Oct. 17, 2008, both of which are hereby incorporated by reference in their entireties.

TECHNICAL FIELD

The present invention relates to a technique for supporting image diagnosis of eye regions.

BACKGROUND ART

Examination on eye regions is widely practiced for the purpose of early diagnosis of life-style related diseases and various kinds of diseases ranking high in causes of blindness. An ocular tomography apparatus such as an OCT (Optical Coherence Tomography) allows three-dimensional observation of the state of the inside of a retinal layer. For this reason, an ocular tomography apparatus is expected to be useful for more accurate diagnosis of diseases.

FIGS. 1A to 1D each are a schematic view of a tomogram of a retinal macular region imaged by an OCT. The OCT three-dimensionally obtains tomograms of eye regions. However, for the sake of descriptive and illustrative simplicity, FIGS. 1A to 1D each two-dimensionally show one cross-section. Referring to FIGS. 1A to 1D, reference numeral 1 denotes a pigmented retinal layer; 2, nerve fiber layer; and 3, an internal limiting membrane. Assume that such a tomogram is input. In this case, measuring the thickness (T2 in FIG. 1A) of the nerve fiber layer 2 makes it possible to quantitatively diagnose the degree of progress of a disease such as glaucoma or the degree of recovery after treatment.

In order to quantitatively measure the thicknesses of these layers, patent reference 1 discloses a technique of detecting the boundaries between the respective retinal layers from a tomogram by using a computer and measuring the thickness of each layer. As shown in, for example, FIG. 1B, this technique detects the internal limiting membrane 3, the nerve fiber layer 2, and the boundary (a nerve fiber layer boundary 4) between the nerve fiber layer 2 and the layer located below it, and measures the thickness of the nerve fiber layer 2.

In a disease such as age-related macular degeneration, the shape of the pigmented retinal layer 1 deforms into a three-dimensional shape in accordance with the condition of the disease. Quantifying the deformation degree of the shape is therefore effective in comprehending the condition of the disease.

FIG. 1C is a schematic view of the layer structure of the retina in age-related macular degeneration. The pigmented retinal layer 1 in age-related macular degeneration has an area which is partly corrugated in the vertical direction. The following method is available as a method of diagnosing age-related macular degeneration using an OCT. This method obtains the area or the sum (volume) of the difference (the hatched portion in FIG. 1D) or differences between a boundary 5 (solid line) of the pigmented retinal layer 1 which is observable on a tomogram and an estimated position 6 (broken line: to be referred to as a normal structure hereinafter) of the boundary of the pigmented retinal layer 1 which is supposed to exist in a normal condition. This quantifies the state of the disease.

In medical checkups or the like, it is desired to detect a plurality of kinds of eye diseases such as glaucoma and age-related macular degeneration by one examination. In contrast to this, in the field using chest CT images and X-ray images, there is disclosed a technique of concurrently executing diagnosis support algorithms corresponding to regions to be analyzed to detect abnormal region candidates, and determining the disease types of abnormal regions.

Note that in this specification, information used for diagnosis of an eye region which is acquired by the above measurement (i.e., values obtained by quantifying the thickness of a predetermined layer and a difference from a normal structure) will be generically termed "eye region diagnosis information data" or simply "diagnosis information data".

Prior Art Reference
Patent Reference
Patent reference 1: Japanese Patent Laid-Open No. 2008-073099
Patent reference 2: Japanese Patent Laid-Open No. 2007-275318

Problems that the Invention is to Solve

The technique described in patent reference 1 does not, however, disclose any layer boundary detection method for the detection of a plurality of kinds of diseases. It is therefore necessary to perform processing by using a fixed analysis method or perform measurement after an operator designates an analysis method suitable for each case. If no proper processing result can be obtained, it is necessary to perform measurement again upon changing the analysis method or parameters for image processing.

According to the technique described in patent reference 2, concurrent execution of a plurality of CAD algorithms involves many wasteful processes, resulting in a needlessly large calculation amount.

The present invention has been made in consideration of the above problems, and has as its object to provide a technique for adaptively acquiring eye region diagnosis information data for diagnosis of a plurality of kinds of diseases from tomograms of an eye region without increasing the load on a user.

More specifically, it is an object of the present invention to provide a technique for detecting lesions corresponding to a plurality of kinds of diseases from tomograms of an eye region and quantitatively analyzing the degrees of progress of the lesions or the degrees of recovery after treatment.

It is another object of the present invention to provide a technique for efficiently detecting lesions and performing quantitative analysis on lesions from tomograms of an eye region.

SUMMARY OF THE INVENTION

In order to achieve the objects of the present invention, for example, an image processing apparatus according to the present invention has the following arrangement.

That is, there is provided an image processing apparatus which processes a tomogram of an eye region, characterized by comprising layer acquisition means for acquiring a predetermined layer area from the tomogram, changing means for changing an algorithm for acquiring, based on information data extracted from the layer area, diagnosis information data as information to be used for diagnosis of the eye region from the tomogram, and means for acquiring the diagnosis information data from the tomogram based on the algorithm changed by the changing means.

In order to achieve the objects of the present invention, for example, an image processing method according to the present invention has the following arrangement.

That is, there is provided an image processing method performed by an image processing apparatus which processes a tomogram of an eye region, characterized by comprising the layer acquisition step of acquiring a predetermined layer area from the tomogram, the changing step of changing an algorithm for acquiring, based on information data extracted from the layer area, diagnosis information data as information to be used for diagnosis of the eye region from the tomogram, and the step of acquiring the diagnosis information data from the tomogram based on the algorithm changed in the changing step.

According to the arrangement of the present invention, it is possible to adaptively acquire eye region diagnosis information data for diagnosis of a plurality of kinds of diseases from tomograms of an eye region without increasing the load on a user.

In addition, it is possible to detect lesions corresponding to a plurality of kinds of diseases from tomograms of an eye region and quantitatively analyze the degrees of progress of lesions and the degrees of recovery after treatment.

Furthermore, it is possible to efficiently detect lesions and perform quantitative analysis on lesions by using tomograms of an eye region.

Other features and advantages of the present invention will be apparent from the following description taken in conjunction with the accompanying drawings, in which like reference characters designate the same or similar parts throughout the figures thereof.

BRIEF DESCRIPTION OF DRAWINGS

The accompanying drawings, which are incorporated in and constitute a part of the specification, illustrate embodiments of the invention and, together with the description, serve to explain the principles of the invention.

FIG. 4 is a flowchart for processing executed by the image processing apparatus 10 according to the first embodiment of the present invention;

FIG. 5 is a flowchart showing the details of processing executed in step S460;

FIG. 6 is a flowchart showing the details of processing executed in step S465;

FIG. 7 is a view showing examples of three types of weighting functions;

DESCRIPTION OF THE INVENTION

[First Embodiment]

Figure 1A:
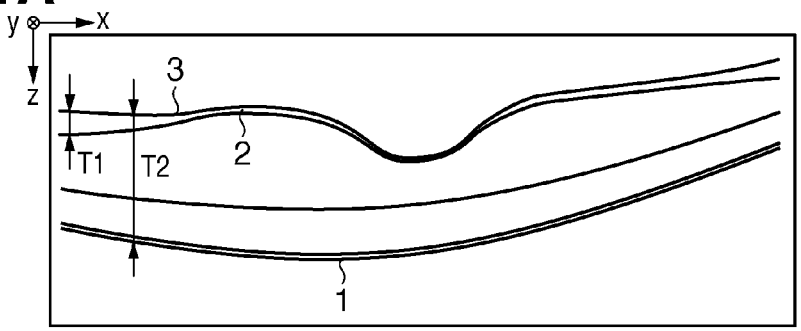
FIG. 1A is a schematic view of a tomogram of a retinal macular region imaged by an OCT.
Figure 1B:
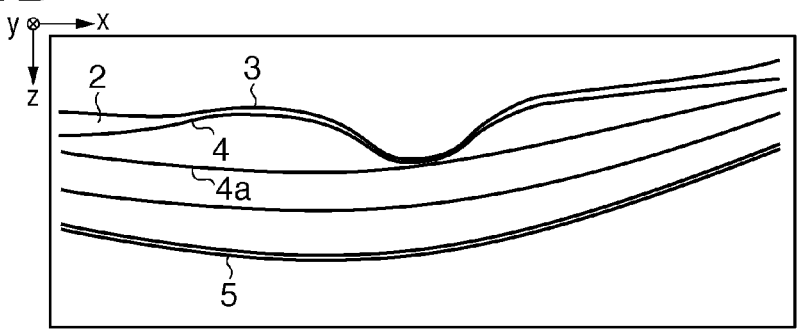
FIG. 1B is a schematic view of a tomogram of the retinal macular region imaged by the OCT.
Figure 1C:
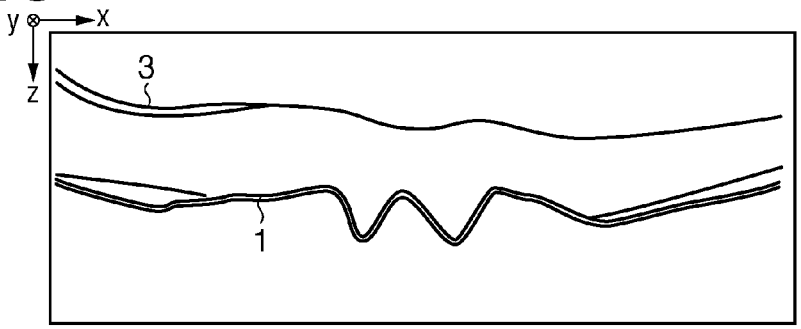
FIG. 1C is a schematic view of a tomogram of the retinal macular region imaged by the OCT.
Figure 1D:
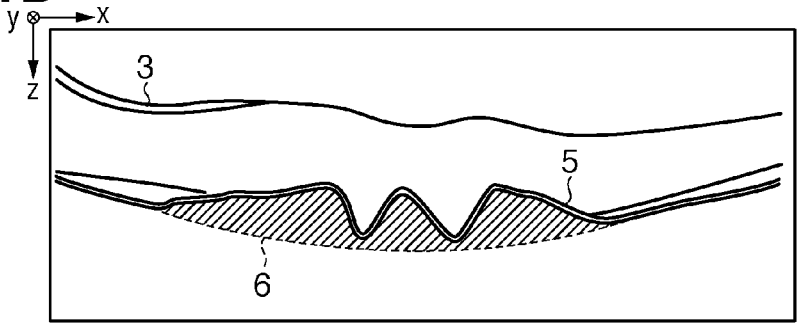
FIG. 1D is a schematic view of a tomogram of the retinal macular region imaged by the OCT.

An image processing apparatus according to this embodiment acquires a tomogram of a macular region of the eye to be examined (an examination target eye), and executes analysis processing for a predetermined layer depicted in the acquired tomogram, thereby quantifying a lesion. If, for example, it is determined by the analysis processing for the predetermined layer that the pigmented retinal layer is normal, the apparatus performs analysis processing for examination of glaucoma or the like. That is, as shown in FIG. 1B, the apparatus detects an internal limiting membrane 3, a nerve fiber layer boundary 4, and a boundary 5 of a pigmented retinal layer 1 (to be referred to as the pigmented retinal layer boundary 5 hereinafter) from a tomogram, and measures the thickness of a nerve fiber layer 2 and the thickness of the overall retinal layer in order to acquire diagnosis information data. If it is determined by analysis processing for a predetermined layer that the pigmented retinal layer 1 is abnormal, the apparatus performs analysis processing for examination of age-related macular degeneration or the like. That is, as shown in FIG. 1D, the apparatus detects the internal limiting membrane 3 and the pigmented retinal layer boundary 5 from the tomogram, and estimates a normal structure 6 of the pigmented retinal layer boundary 5. The apparatus then measures the thickness of the overall retinal layer as diagnosis information data, and quantifies the disturbance of the pigmented retinal layer 1.

This embodiment will exemplify a case in which the pigmented retinal layer 1 is measured. However, it is possible to perform measurement by using other retinal deep layer boundaries (external limiting membrane (not shown), a visual cell inner segment/outer segment boundary (not shown), and the inner layer side boundary of a pigmented retinal layer (not shown), and the like) in place of the pigmented retinal layer boundary 5.

In addition, the same diagnosis information data can be obtained by measuring the distance between the internal limiting membrane 3 and an outer layer side boundary 4a of an inner plexiform layer instead of the distance between the internal limiting membrane 3 and the nerve fiber layer boundary 4.

Each subsequent embodiment including this embodiment will exemplify a case in which the thickness of a nerve fiber layer is measured. However, it is possible to measure the outer layer side boundary 4a of an inner plexiform layer instead of the nerve fiber layer boundary 4.

Figure 2:
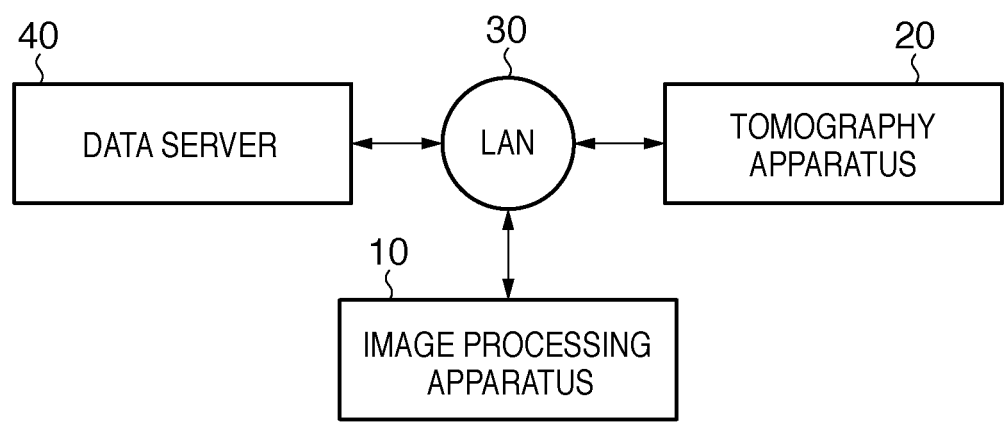
FIG. 2 is a block diagram showing an example of the arrangement of a system including an image processing apparatus according to the first embodiment of the present invention.

FIG. 2 is a block diagram showing an example of the arrangement of a system including the image processing apparatus according to this embodiment. As shown in FIG. 2, an image processing apparatus 10 as the image processing apparatus according to this embodiment is connected to a tomography apparatus 20 and a data server 40 via a local area network (LAN) 30 such as Ethernet®. Note that the connection between the respective devices is not limited to connection via a LAN, but can be connection via an interface such as USB or IEEE1394. Alternatively, this connection may be connection via an external network such as the Internet.

The tomography apparatus 20 is an apparatus which obtains a tomogram of an eye region, and includes, for example, a time domain OCT or a Fourier domain OCT. In accordance with the operation of an operator, the tomography apparatus 20 three-dimensionally obtains a tomogram of a macular region of the eye to be examined. The tomography apparatus 20 then transmits the obtained tomogram to the image processing apparatus 10 via the LAN 30.

The data server 40 is a server which holds a tomogram of the eye to be examined, the analysis result (e.g., a layer boundary and the quantified numerical data) obtained by the image processing apparatus 10 based on the tomogram, and normal eye data (e.g., the normal range of layer thicknesses). The image processing apparatus 10 controls the storage of data in the data server 40. For example, the image processing apparatus 10 stores, in the data server 40, the tomogram received from the tomography apparatus 20 without any change or upon performing some process for the tomogram or the result of analysis processing performed by using the tomogram. In addition, the data server 40 transmits various past data concerning the eye to be examined to the image processing apparatus 10, as needed, in accordance with a request from the image processing apparatus 10.

Figure 3:
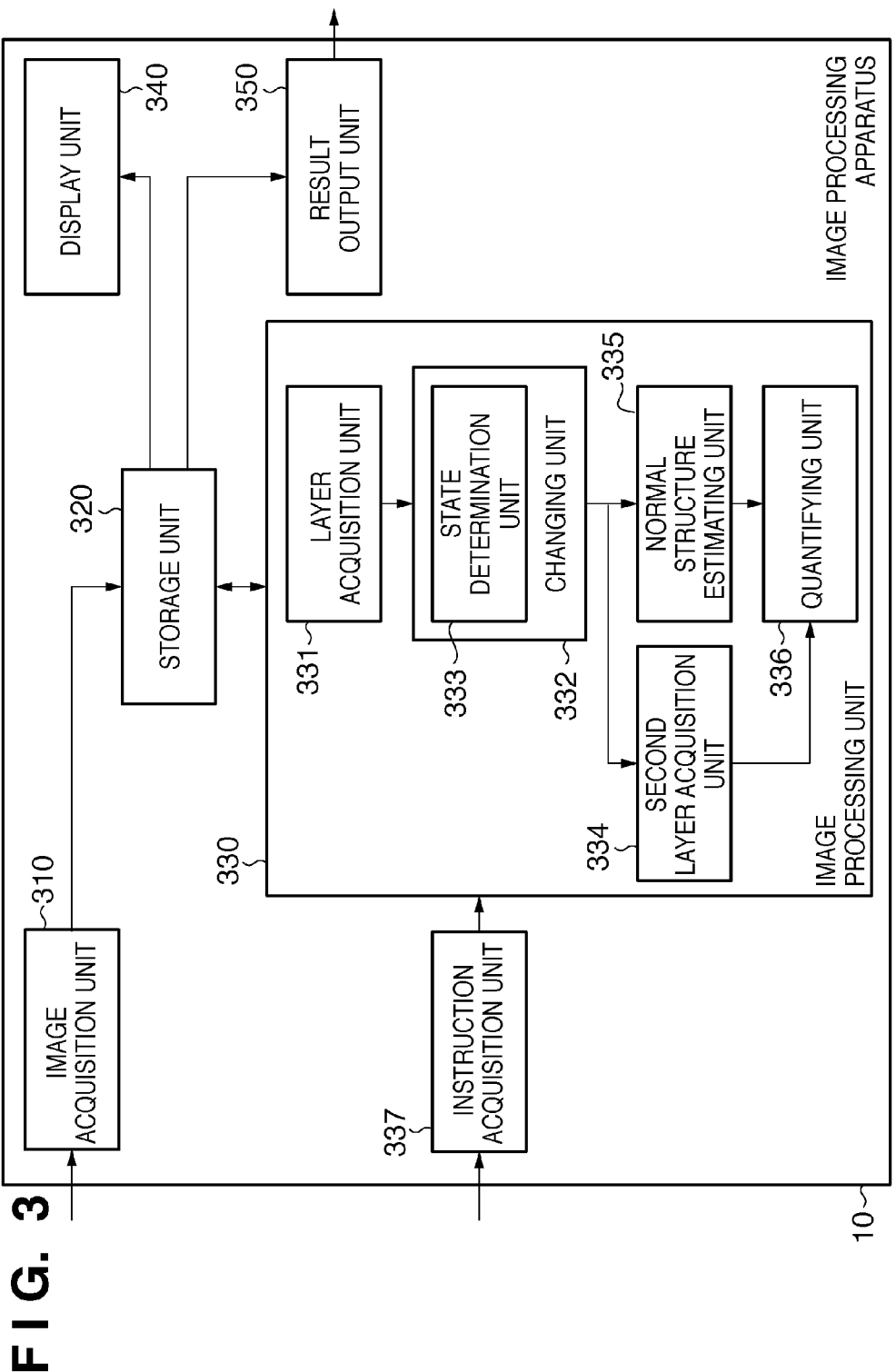
FIG. 3 is a block diagram showing an example of the functional arrangement of an image processing apparatus 10.

The functional arrangement of the image processing apparatus 10 according to this embodiment will be described next with reference to FIG. 3. FIG. 3 is a block diagram showing an example of the functional arrangement of the image processing apparatus 10. As shown in FIG. 3, the image processing apparatus 10 includes an image acquisition unit 310, a storage unit 320, an image processing unit 330, a display unit 340, a result output unit 350, and an instruction acquisition unit 337.

The image acquisition unit 310 issues a request to the tomography apparatus 20 to transmit a tomogram and also receives (acquires) the tomogram transmitted by the tomography apparatus 20 in accordance with the request. Note that if the tomography apparatus 20 holds information identifying the eye to be examined, e.g., the identification number of an object or an identifier indicating whether an examination target is the right or left eye, the image acquisition unit 310 may acquire this information from the tomography apparatus 20, together with the tomogram. Assume that in the following description, the tomogram acquired by the image acquisition unit 310 is attached with various parameters concerning tomography as information.

The storage unit 320 temporarily holds the tomogram acquired by the image acquisition unit 310. In addition, the storage unit 320 temporarily holds the analysis result on the tomogram which is obtained by the image processing unit 330. Data held in the storage unit 320 is sent to the image processing unit 330, the display unit 340, and the result output unit 350, as needed.

The image processing unit 330 acquires a tomogram held in the storage unit 320, and determines the state of a predetermined layer depicted on the tomogram. The image processing unit 330 narrows down to a disease candidate in accordance with the result and executes image processing suitable for the disease. The image processing unit 330 includes a layer acquisition unit 331, a changing unit 332, a second layer acquisition unit 334, a normal structure estimating unit 335, and a quantifying unit 336.

The layer acquisition unit 331 detects predetermined layers (layer areas) such as the internal limiting membrane 3 and the pigmented retinal layer boundary 5 from the tomogram acquired from the storage unit 320. The contents of specific processing executed by the layer acquisition unit 331 will be described in detail later.

The changing unit 332 includes a state determination unit 333. The state determination unit 333 determines the state of a predetermined layer detected by the layer acquisition unit 331. The changing unit 332 changes an image analysis algorithm in accordance with the state determination result obtained by the state determination unit 333, and informs each unit of the corresponding information. The contents of specific processing executed by the changing unit 332 will be described in detail later.

If the state determination unit 333 determines that the pigmented retinal layer 1 is normal, the second layer acquisition unit 334 detects the nerve fiber layer boundary 4 as the second layer (the second layer area) from the tomogram in accordance with the processing contents designated by the changing unit 332. The contents of specific processing executed by the second layer acquisition unit 334 will be described in detail later.

If the state determination unit 333 determines that the pigmented retinal layer 1 is abnormal, the normal structure estimating unit 335 estimates the normal structure (the normal structure 6 in FIG. 1D) of the pigmented retinal layer boundary 5 in accordance with the processing contents designated by the changing unit 332. In contrast, if the state determination unit 333 determines that the pigmented retinal layer 1 is normal, the normal structure estimating unit 335 executes no processing in accordance with an instruction from the changing unit 332. The contents of specific processing executed by the normal structure estimating unit 335 will be described in detail later.

The quantifying unit 336 quantifies the thickness of the overall retinal layer from the predetermined layer detected by the layer acquisition unit 331. If the nerve fiber layer boundary 4 has been detected by the second layer acquisition unit 334, the quantifying unit 336 quantifies the thickness of the nerve fiber layer 2. If the normal structure estimating unit 335 has estimated the normal structure 6 of the pigmented retinal layer boundary 5, the quantifying unit 336 quantifies the difference between the pigmented retinal layer boundary 5 detected by the layer acquisition unit 331 and the normal structure 6 estimated by the normal structure estimating unit 335 (i.e., the disturbance of the pigmented retinal layer 1). The contents of specific processing executed by the quantifying unit 336 will be described in detail later.

The display unit 340 displays the tomogram upon superimposing information concerning the layer boundaries and normal structure obtained by the image processing unit 330. The display unit 340 also displays various kinds of quantified numerical data.

The result output unit 350 associates an examination date, information identifying the eye to be examined, a tomogram of the eye to be examined, and the analysis result obtained by the image processing unit 330, and transmits the resultant information as information to be stored to the data server 40.

The instruction acquisition unit 337 receives an externally input instruction (e.g., an instruction input by the user), and sends it to the image processing unit 330 on the subsequent stage.

Note that all the units shown in FIG. 3 can be implemented by hardware, or the units other than the storage unit 320 and the display unit 340 can be implemented by software. In either case, a similar apparatus can be implemented. In the latter case, the software is installed in a memory in a computer including the storage unit 320 and the display unit 340 as hardware. The CPU of this computer executes this software to implement an apparatus similar to the apparatus in which the respective units are implemented by hardware.

Figure 15:
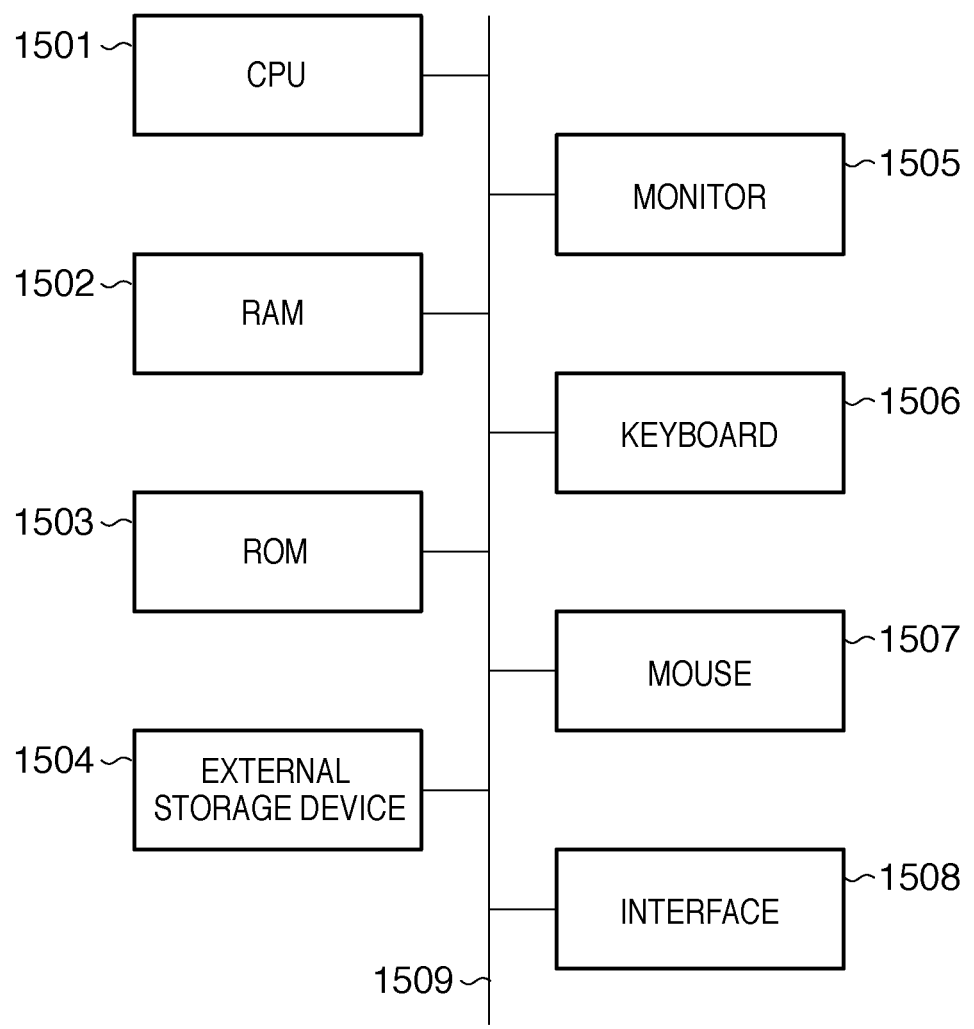
FIG. 15 is a block diagram showing an example of the hardware arrangement of a computer which has hardware corresponding to a storage unit 320 and a display unit 340 and holds and executes the remaining units as software.

FIG. 15 is a block diagram showing an example of the hardware arrangement of the computer which includes hardware corresponding to the storage unit 320 and the display unit 340, and holds and executes the remaining units as software.

A CPU 1501 controls the overall computer by using programs and data stored in a RAM 1502 and a ROM 1503, and executes each process (to be described later) as a process performed by the image processing apparatus 10.

The RAM 1502 has an area for temporarily storing the program and data loaded from an external storage device 1504 and a work area necessary for the execution of various kinds of processes by the CPU 1501. That is, the RAM 1502 can provide various kinds of areas, as needed. The storage unit 320 shown in FIG. 3 can be implemented by the RAM 1502.

The ROM 1503 generally stores a BIOS for the computer, set data, and the like.

The external storage device 1504 is a device serving as a large-capacity information storage device such as a hard disk drive. The external storage device 1504 stores an OS (Operating System) and computer programs and data for causing the CPU 1501 to execute the respective processes to be described later as processes performed by the image processing apparatus 10. The computer programs include computer programs for causing the CPU 1501 to implement the functions of the image acquisition unit 310, image processing unit 330, result output unit 350, and instruction acquisition unit 337. Assume that this data includes data handled as known information (information generated in advance) in the following description. The computer programs and data stored in the external storage device 1504 are loaded into the RAM 1502 as needed under the control of the CPU 1501. The CPU 1501 is to execute these programs.

A monitor 1505 includes a liquid crystal display and the like. The display unit 340 shown in FIG. 3 can be implemented by the monitor 1505.

A keyboard 1506 and a mouse 1507 each are used as an example of an input device. The user can input various kinds of instructions to the CPU 1501 by using such an input device. Note that a computer program corresponding to the instruction acquisition unit 337 notifies the CPU 1501 of various instructions input by using this input device.

An interface 1508 serves to exchange various data between the image processing apparatus 10 and an external device, and includes IEEE1394, USB, Ethernet port, and the like. The data acquired via the interface 1508 is stored in the RAM 1502 and the external storage device 1504. The image acquisition unit 310 and the result output unit 350 exchange data via the interface 1508.

The above respective units are connected to a bus 1509.

Specific processing executed by the image processing apparatus 10 of this embodiment will be described next with reference to the flowchart of FIG. 4. For easy understanding, in the following description, each unit shown in FIG. 3 serves as an entity in processing. In practice, however, the CPU 1501 which executes computer programs corresponding to these units serves as an entity in processing. Obviously, in addition, computer programs and data which are necessary for the execution of the following processing have already been loaded from the external storage device 1504 into the RAM 1502 before the start of the processing based on the flowchart of FIG. 4.

<Step S410>

In step S410, the image acquisition unit 310 transmits an acquisition request for a tomogram to the tomography apparatus 20. Upon receiving this acquisition request, the tomography apparatus 20 transmits a tomogram corresponding to the request. The image acquisition unit 310 therefore receives this tomogram transmitted from the tomography apparatus 20 via the LAN 30. The image acquisition unit 310 then stores the received tomogram in the storage unit 320.

<Step S420>

In step S420, the display unit 340 displays the tomogram stored in the storage unit 320 in step S410. For example, an image like that schematically shown in FIG. 1A or 1C is displayed. In this case, since the tomogram is three-dimensional data, the tomogram actually displayed on the display unit 340 is a two-dimensional tomogram obtained by cutting a cross-section of interest from the three-dimensional data. It is preferable to arbitrarily select a cross-section to be displayed via a GUI or the like. It is also possible to display various data (a tomogram and its analysis result) obtained by imaging in the past side by side.

<Step S430>

In step S430, the layer acquisition unit 331 acquires the tomogram stored in the storage unit 320 in step S410. The layer acquisition unit 331 detects the internal limiting membrane 3 and the pigmented retinal layer boundary 5 from this tomogram. The layer acquisition unit 331 detects the coordinates of a central fossa as the center of a macular region from this tomogram. The layer acquisition unit 331 stores each piece of information detected in this manner in the storage unit 320.

Specific processing for the detection of layer boundaries will be described below. In this case, a three-dimensional tomogram as a processing target is regarded as a set of two-dimensional tomograms (B-scan images), and the following processing is executed for each of the two-dimensional tomograms.

First of all, smoothing filter processing is performed for a two-dimensional tomogram of interest to remove noise components. Edge components are then extracted from the two-dimensional tomogram, and several line segments are extracted as layer boundary candidates based on the connectivity of the edge components. The uppermost line segment is selected as the internal limiting membrane 3 from these candidates. The lowermost line segment is selected as the pigmented retinal layer boundary 5.

In addition, it is possible to improve the detection accuracy by using a deformable model such as a Snakes model or a level set method model using these line segments as initial values. It is also possible to detect layer boundaries by using a technique like a graph cut method. Note that boundary detection using a deformable model or graph cut can be three-dimensionally performed for a three-dimensional tomogram as a target. Alternatively, it is possible to regard a three-dimensional tomogram as a set of two-dimensional tomograms and two-dimensionally apply the above technique for each of the two-dimensional tomograms. Note that methods of detecting layer boundaries are not limited to these methods, and it is possible to use any method as long as it can detect layer boundaries from a tomogram of an eye region.

The layer acquisition unit 331 further detects the coordinates of a central fossa by using the internal limiting membrane 3. More specifically, the layer acquisition unit 331 sets, as the coordinate position of the central fossa, a coordinate position near the center of the tomogram at which the z-coordinate of the detected internal limiting membrane 3 is maximized.

<Step S440>

In step S440, the state determination unit 333 determines, based on the pigmented retinal layer boundary 5 detected by the layer acquisition unit 331 in step S430, whether the pigmented retinal layer 1 is normal. The state determination unit 333 then outputs the determination result to the storage unit 320. If, for example, the maximum value of the curvature of a control point sequence constituting the detected pigmented retinal layer 5 is equal to or more than a predetermined threshold or the minimum value of the angle is equal to or less than a predetermined threshold, the state determination unit 333 determines that the pigmented retinal layer 1 is abnormal.

Note that it is possible to determine whether the pigmented retinal layer 1 is normal, by determining whether the number of extreme values of the pigmented retinal layer boundary 5 is equal to or more than a threshold, or based on a statistics such as the number of inflection points or the variance of curvatures. These processes may be performed for only the pigmented retinal layer boundary 5 near the central fossa at which abnormality tends to occur.

<Step S450>

In step S450, the changing unit 332 causes the process to branch in accordance with the determination result obtained by the state determination unit 333 in step S440 (i.e., changes the algorithm). If the determination result in step S440 indicates "normal", the changing unit 332 instructs the second layer acquisition unit 334 to execute the corresponding processing. The process then advances to step S460.

In contrast, if the determination result in step S440 indicates "abnormal", the changing unit 332 instructs the normal structure estimating unit 335 to execute the corresponding processing. The process then advances to step S465.

<Step S460>

In step S460, the image processing unit 330 executes analysis processing to be performed when a predetermined layer is normal. The display unit 340 also displays the analysis result. The processing in this step will be described in detail later with reference to the flowchart shown in FIG. 5.

<Step S465>

In step S465, the image processing unit 330 executes analysis processing to be performed when a predetermined layer is abnormal. The display unit 340 also displays the analysis result. The processing in this step will be described in detail later with reference to the flowchart shown in FIG. 6.

<Step S470>

In step S470, the instruction acquisition unit 337 externally acquires an instruction to store or not to store the current processing result on the eye to be examined in the data server 40. This operator inputs this instruction via the keyboard 1506 or the mouse 1507. If the operator inputs a storage instruction, the process advance to step S480. If the operation does not input a storage instruction, the process advances to step S490.

<Step S480>

In step S480, the result output unit 350 associates an examination date and time, information identifying the eye to be examined, a tomogram of the eye to be examined, and the analysis result obtained by the image processing unit 330, and transmits the resultant information as information to be stored to the data server 40.

<Step S490>

In step S490, the instruction acquisition unit 337 externally acquires an instruction to end or not to end the analysis processing for the tomogram by the image processing apparatus 10. The operator inputs this instruction via the keyboard 1506 or the mouse 1507. If the operator inputs an instruction to end the processing, the image processing apparatus 10 ends the processing. If the operator inputs an instruction to continue the processing, the process returns to step S410 to execute the next processing for the eye to be examined (or re-processing for the same eye to be examined).

The details of processing executed in step S460 will be described next with reference to FIG. 5.

<Step S510>

In step S510, the second layer acquisition unit 334 acquires the nerve fiber layer boundary 4 from the tomogram. As a method of acquiring the nerve fiber layer boundary 4, it is conceivable to use, for example, a method of scanning in the positive direction of the z-axis from the z-coordinate value of the internal limiting membrane 3 and connecting points at which luminance values or edges are equal to or more than a threshold.

<Step S520>

In step S520, the quantifying unit 336 quantifies the thickness of the nerve fiber layer 2 and the thickness of the overall retinal layer based on the nerve fiber layer boundary 4 acquired in step S510. First of all, the quantifying unit 336 calculates the thickness of the nerve fiber layer 2 (T1 in FIG. 1A) on each coordinate point on an x-y plane by obtaining the difference in z-coordinate between the nerve fiber layer boundary 4 and the internal limiting membrane 3. Likewise, the quantifying unit 336 calculates the thickness of the overall retinal layer (T2 in FIG. 1A) by obtaining the difference in z-coordinate between the pigmented retinal layer boundary 5 and the internal limiting membrane 3. The quantifying unit 336 also calculates the areas of the respective layers (the nerve fiber layer 2 and the overall retinal layer) at the respective cross-sections by adding the layer thicknesses at the respective coordinate points in the x-axis direction for the respective y-coordinates. In addition, the quantifying unit 336 calculates the volume of each layer by adding the obtained areas in the y-axis direction. These results are then stored in the storage unit 320.

<Step S530>

In step S530, the display unit 340 displays the nerve fiber layer boundary 4 detected in step S510 upon superimposing it on the tomogram. When the boundaries between the layers are indicated by lines, as shown in FIG. 1B, it is preferable to use lines of predetermined colors for the respective boundaries. For example, red, yellow, and green lines are used for the internal limiting membrane 3, the nerve fiber layer boundary 4, and the pigmented retinal layer boundary 5, respectively, to present them. Alternatively, it is possible to present layer boundaries, without explicitly indicating them, by adding translucent colors to the layer areas. For example, it is possible to present the nerve fiber layer 2 and the overall retinal layer while coloring an area indicating the overall retinal layer except for the nerve fiber layer 2 in green and coloring an area indicating the nerve fiber layer 2 in red. When displaying them, it is preferable to use an arrangement that allows to select a cross-section of interest via a GUI or the like. It is also possible to three-dimensionally display a tomogram as three-dimensional data by using a known volume rendering technique.

The display unit 340 further displays information concerning the layer thicknesses quantified in step S520. In this case, the display unit 340 may present the information as a layer thickness distribution map about the overall three-dimensional tomogram (x-y plane) or may display the area of each layer on a cross-section of interest in conjunction with the display of the above detection result. Alternatively, it is possible to display the overall volume or calculate and display the volume of an area designated on an x-y plane by the operator.

Executing the processing from step S510 to step S530 described above will implement the processing in step S460 described above. Note that in this embodiment, in step S460, only the thicknesses of the nerve fiber layer 2 and the overall retinal layer are checked. However, it is possible to analyze other layers such as a visual cell layer and an external limiting membrane.

The details of the processing executed in step S465 will be described next with reference to FIG. 6.

<Step S610>

In step S610, the normal structure estimating unit 335 estimates the normal structure 6 from the pigmented retinal layer boundary 5 acquired in step S430. The following will exemplify a case in which a three-dimensional tomogram input as a processing target is regarded as a set of two-dimensional tomograms (B-scan images), and the normal structure of each of the two-dimensional tomograms is estimated. More specifically, the normal structure estimating unit 335 estimates the normal structure 6 by applying a quadratic function to a coordinate point group representing the pigmented retinal layer boundary 5 acquired in each two-dimensional tomogram. Letting $\epsilon i$ be the difference between a z-coordinate $zi$ of the ith point of the layer boundary data of the pigmented retinal layer boundary 5 and a z-coordinate $z'i$ of the ith point of the data of the normal structure 6, an evaluation equation for obtaining an approximation function is expressed as follows:

$$M = \min \Sigma \rho(\epsilon i)$$

where $\Sigma$ represents the total sum of i, and $\rho(\ )$ is a weighting function. FIG. 7 shows examples of three types of weighting functions. Referring to FIG. 7, the abscissa represents x, and the ordinate represents $\rho(x)$. Weighting functions to be used are not limited to those shown in FIG. 7, and any types of functions can be set. In the above equation, a function is estimated so as to minimize an evaluation value M.

This method described above is the method of regarding an input three-dimensional tomogram as a set of two-dimensional tomograms (B-scan images) and estimating the normal structure 6 with respect to each of the two-dimensional tomograms. However, the method of estimating the normal structure 6 is not limited to this method, and a three-dimensional tomogram can be directly processed. In this case, it is possible to perform ellipse fitting for the three-dimensional coordinate point group of the layer boundary acquired in step S430 using the same selection criterion for a weighting function as that used in the above case. In addition, the shape to which the normal structure 6 is approximated is not limited to a quadratic function, and estimation can be made by using a function with another degree.

<Step S620>

In step S620, the quantifying unit 336 quantifies the thickness of the overall retinal layer based on the layer boundary acquired in step S430. The quantifying unit 336 also quantifies the disturbance of the pigmented retinal layer 1 based on the difference between the pigmented retinal layer boundary 5 acquired in step S430 and the normal structure 6 estimated in step S610. Although the quantifying unit 336 quantifies the thickness of the overall retinal layer, since this processing is the same as that in step S520, a detailed description of the processing will be omitted. These results are then stored in the storage unit 320.

A feature amount representing the disturbance of the pigmented retinal layer 1 can be anything as long as it is possible to quantify the difference between the acquired pigmented retinal layer boundary 5 and the normal structure 6. For example, it is possible to obtain, as a feature of an area corresponding to a difference, a statistics of the obtained difference (thickness) (e.g., a distribution, a maximum value, an average value, a median, a variance, a standard deviation, or the number or ratio of points equal to or more than a threshold). Alternatively, as a feature of a difference area, it is possible to obtain a density feature such as a density histogram, average density value, density variance, or contrast.

<Step S630>

In step S630, the display unit 340 superimposes and displays the pigmented retinal layer boundary 5 acquired in step S430 and the normal structure 6 estimated in step S610. In addition, in accordance with this information, the display unit 340 displays the information quantified in step S620. This display processing is the same as the processing in step S530, and hence a detailed description will be omitted.

Executing the processing from step S610 to step S630 described above will implement the processing in step S465.

As described above, according to this embodiment, the image processing apparatus 10 determines whether the pigmented retinal layer 1 of the eye to be examined is normal, and acquires diagnosis information data suitable for each case. That is, if the pigmented retinal layer 1 is normal, the image processing apparatus 10 measures not only the thickness of a retinal layer but also the thickness of the nerve fiber layer 2 as diagnosis information data of the eye region. If the pigmented retinal layer 1 is abnormal, the image processing apparatus 10 quantifies the disturbance of the shape of the pigmented retinal layer 1 as diagnosis information data of the eye region. As a consequence, it is possible to adaptively acquire diagnosis information data of the eye region which is used for the diagnosis of a plurality of kinds of diseases from a tomogram of the eye region without increasing the load on the user.

(First Modification)

This embodiment performs acquisition and measurement of a layer and second layer of a macular region. However, a target region whose layers are to be acquired and measured is not limited to a macular region. For example, acquisition of layers may be performed with respect to an optic papilla.

Figure 8A:
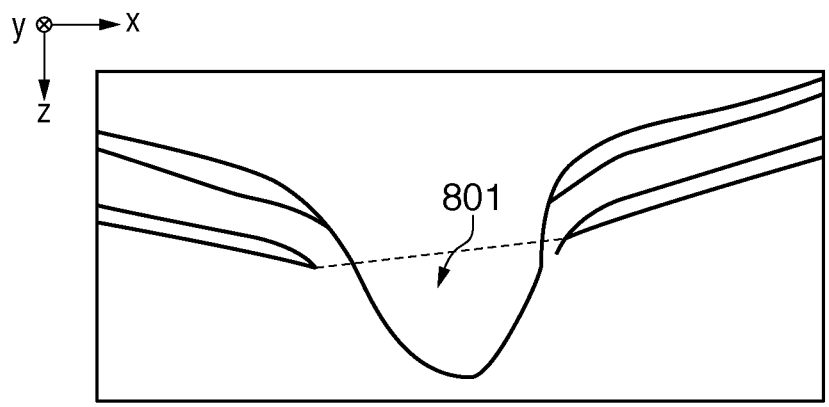
FIG. 8A is a view showing an example of an optic papilla.
Figure 8B:
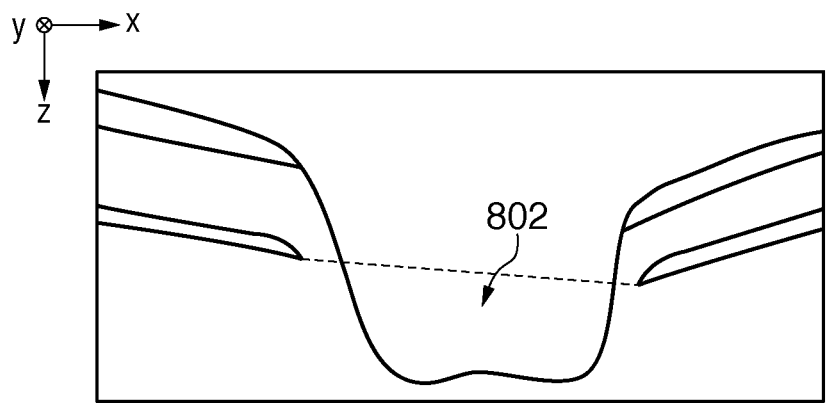
FIG. 8B is a view showing an example of the optic papilla.

Assume that after layers of the macular region are acquired, the state determination unit 333 determines that the retinal deep layer is normal. In this case, the second layer of the optic papilla is acquired. It is possible to measure the thickness of the nerve fiber layer or indexes 801 and 802 indicating indentation shapes of the optic papilla as shown in FIGS. 8A and 8B (e.g., the areas or volumes of the indentations).

(Second Modification)

In this embodiment, when the internal limiting membrane 3 and the pigmented retinal layer boundary 5 are acquired in step S430 and the state determination unit 333 determines that they are normal, the nerve fiber layer boundary 4 is acquired in step S460. The layer acquisition unit 331 can acquire these layers altogether. That is, it is possible to acquire the internal limiting membrane 3, the nerve fiber layer boundary 4, and the pigmented retinal layer boundary 5 in step S430 and make the second layer acquisition unit 334 perform nothing (or make the image processing unit 330 not include the second layer acquisition unit 334).

The layer acquisition unit 331 acquires the internal limiting membrane 3, the nerve fiber layer boundary 4, and the pigmented retinal layer boundary 5 by the following method. For example, the layer acquisition unit 331 selects the uppermost line segment from several layer boundary candidates detected based on the edge information of a tomogram as the internal limiting membrane 3. The layer acquisition unit 331 also selects a line segment located immediately below the internal limiting membrane 3 as the nerve fiber layer boundary 4. The layer acquisition unit 331 further selects the lowermost line segment as the pigmented retinal layer boundary 5.

(Third Modification)

The method of causing the changing unit 332 to change an image processing algorithm is not limited to the above example. For example, it is possible to prioritize image processing modes (image processing parameters or disease candidates which can be processed) according to the retinal deep layer state obtained by the state determination unit 333 so as to allow the operator to perform selection. More specifically, for example, the display unit 340 displays a list such that when it is determined that the retinal deep layer state is abnormal, a high priority level is assigned to a processing mode for an abnormal retinal deep layer, and a low priority level is assigned to a processing mode for a normal retinal deep layer. This allows the operator to select an image processing mode via the instruction acquisition unit 337. In this case, if the operator issues no instruction, an image processing mode with a high priority level may be automatically executed.

(Fourth Modification)

In this embodiment, the image processing algorithm determined by the changing unit 332 is applied to only a tomogram of an eye region. However, the present invention is not limited to this. For example, when the image processing apparatus 10 further includes a fundus image acquisition unit which acquires a fundus image by using a fundus camera to obtain diagnosis information data of an eye region by using a fundus image and a tomogram, the changing unit 332 may change the image processing algorithm for fundus images. If, for example, a retinal deep layer has fine indentations and the retinal deep layer state obtained by the state determination unit 333 is near the boundary between normality and abnormality, it is possible to issue an instruction to perform, for a fundus image, the processing of checking the presence/absence of a feature indicating the abnormality of the retinal deep layer (an instruction to change the algorithm). That is, it is possible to make the display unit 340 perform display to prompt an operator to check the presence/absence of drusen from a fundus image or perform, for a fundus image, the processing of detecting drusen by using the image processing technique disclosed in the following reference:

"Takuro Iwasaki et al., "An automatic extraction procedure of Drusen region in the fundus image", IEICE technical report, MI2003-10, pp. 17-22, 2004"

[Second Embodiment]

The image processing apparatus 10 according to the first embodiment causes the state determination unit 333 to determine a layer state, and determines an image processing algorithm in accordance with the determination result. An image processing apparatus 10 according to the second embodiment is the same as the first embodiment in that a state determination unit 333 determines a layer state. Note, however, that this embodiment differs from the first embodiment in that an assumed case is diabetic macular edema, and the state determination unit 333 performs layer state determination a plurality of number of times.

Figure 9:
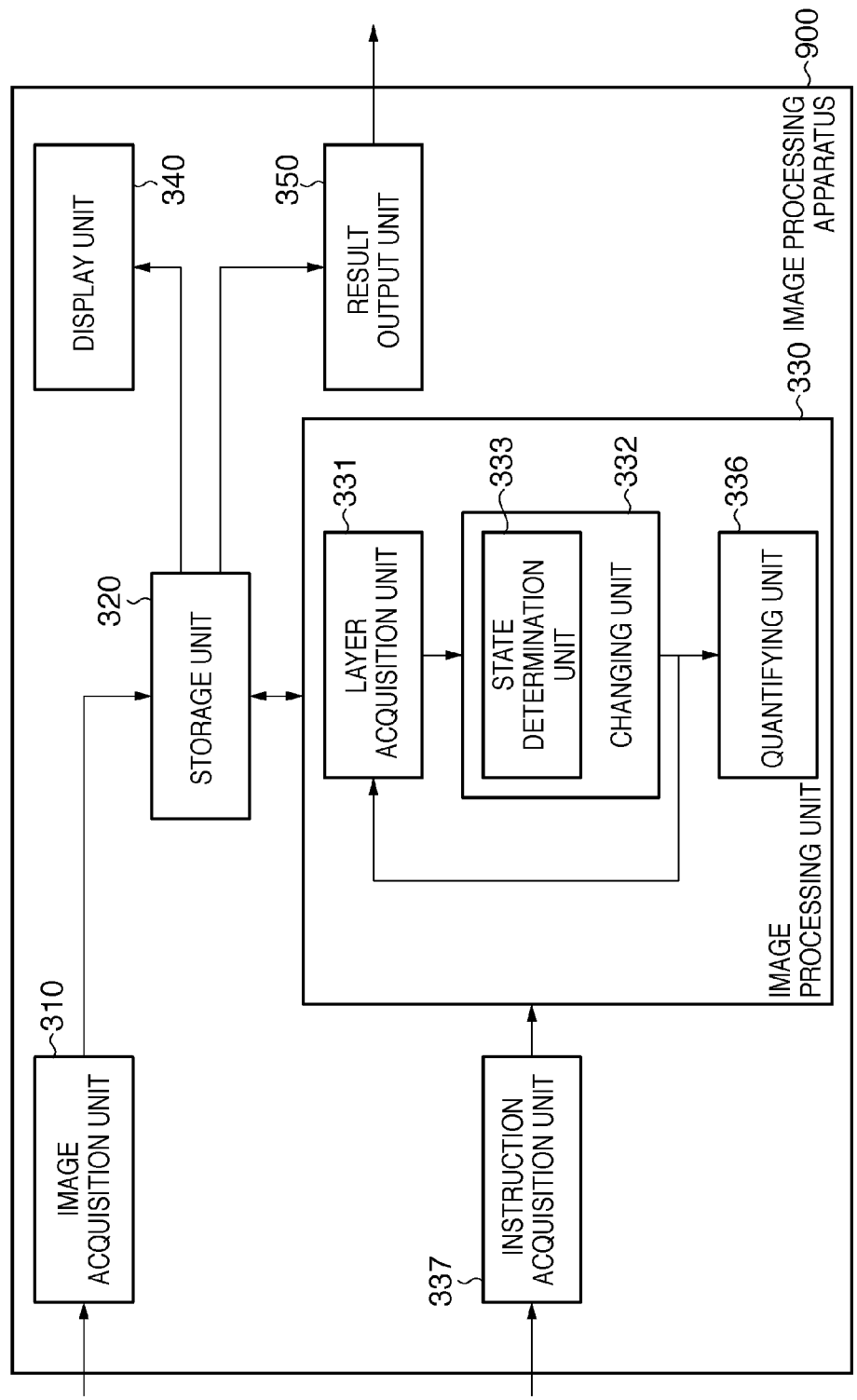
FIG. 9 is a block diagram showing an example of the functional arrangement of an image processing apparatus 900 as an image processing apparatus according to the first embodiment of the present invention.

FIG. 9 is a block diagram showing an example of the functional arrangement of an image processing apparatus 900 as an image processing apparatus according to this embodiment. The arrangement shown in FIG. 9 is obtained by omitting the second layer acquisition unit 334 and the normal structure estimating unit 335 from the arrangement shown in FIG. 3. The remaining arrangement is the same as that in the first embodiment. In addition, the arrangement of a system including the image processing apparatus 900 is the same as that in the first embodiment.

Figure 10:
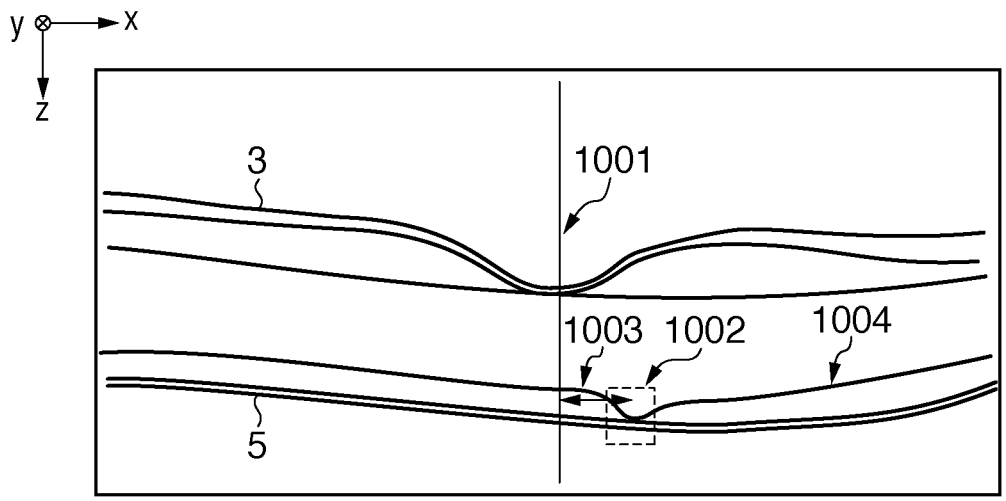
FIG. 10 is a view for explaining the contents of image processing in the second embodiment of the present invention.

The contents of image processing in this embodiment will be described next with reference to FIG. 10.

In the case of macular edema, the retinal layer thickness exhibits an abnormal value, and hence a retinal layer thickness is measured on a tomogram of an eye region. In some macular edema cases, a visual cell layer may have a defect 1002. Checking the presence/absence of a visual cell defect may be effective. In addition, the closer a defect region of a visual cell layer to a central fossa 1001, the higher the possibility that it will hinder visual recovery. When a defect region has occurred, it may be effective to perform measurement at a distance 1003 from the central fossa 1001 of the defective region (a distance in the x-axis direction).

Note that a visual cell layer is adjacent to the upper portion of a pigmented retinal layer, and to be precise, ranges from an external limiting membrane 1004 to the upper side of the pigmented retinal layer. However, it is difficult for any existing ocular tomography apparatus to visually check or recognize an external limiting membrane. For this reason, this embodiment acquires a boundary called a visual cell inner segment/outer segment boundary (not shown) existing slightly below an external limiting membrane in place of the external limiting membrane when measuring a visual cell layer thickness, and measures the thickness between the visual cell inner segment/outer segment boundary and the pigmented retinal layer. Obviously, in the case of a tomogram of an eye region exhibiting a high resolution in an x-z plane, it is possible to directly measure an external limiting membrane. Assume that the data of a retinal layer thickness and the normal value range of visual cell layer thicknesses have been loaded from a data server 40 into a storage unit 320 in advance.

Specific processing performed by the image processing apparatus 900 basically follows the flowchart shown in FIG. 4, but differs only in the following point.

<Step S430>

In step S430, a layer acquisition unit 331 detects an internal limiting membrane 3 and a pigmented retinal layer 5 from a tomogram.

<Step S440>

In step S440, the state determination unit 333 determines, based on the internal limiting membrane 3 and the pigmented retinal layer 5 detected in step S430, whether the thickness of a retinal layer is normal. More specifically, first of all, the state determination unit 333 acquires data indicating the normal value range of retinal layer thicknesses from the storage unit 320. The state determination unit 333 checks whether the distance between the internal limiting membrane 3 and the pigmented retinal layer 5 acquired in step S430 falls within the normal value range. If the distance falls within the normal value range, the state determination unit 333 determines that the layer thickness is normal. If the distance falls outside the normal value range, the state determination unit 333 determines that the layer thickness is abnormal.

<Step S450>

In step S450, the changing unit 332 causes the process to branch in accordance with the determination result obtained in step S440 (i.e., changes the algorithm). That is, if it is determined that the retinal layer thickness is "normal", the changing unit 332 instructs the quantifying unit 336 to execute processing (the process advances to step S460). If it is determined that the retinal layer thickness is abnormal, the changing unit 332 instructs the layer acquisition unit 331 to execute processing (the process advances to step S465).

<Step S460>

Figure 11:
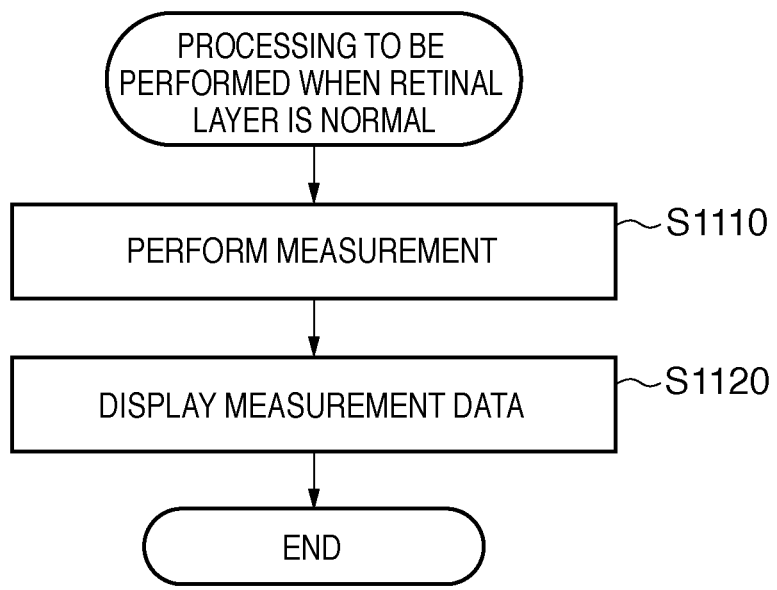
FIG. 11 is a flowchart showing the details of processing in step S460 according to the second embodiment of the present invention.

Step S460 is processing to be performed when a retinal layer thickness is normal. The details of the processing in this step will be described with reference to FIG. 11.

<Step S1110>

In step S1110, a quantifying unit 336 measures the thickness of an overall retinal layer based on the layer boundaries acquired by the layer acquisition unit 331. Note that the retinal layer thickness measurement in step S1110 is the same as that in step S520, and hence a detailed description of this step will be omitted.

<Step S1120>

In step S1120, a display unit 340 superimposes and displays the retinal layer thickness acquisition result in step S1110 and the tomogram. Note that the processing in step S1120 is the same as the display processing for the retinal layer thickness in step S530, and hence a detailed description of the processing in this step will be omitted.

Executing the processing in steps S1110 and S1120 described above can implement the processing in step S460.

<Step S465>

Figure 12:
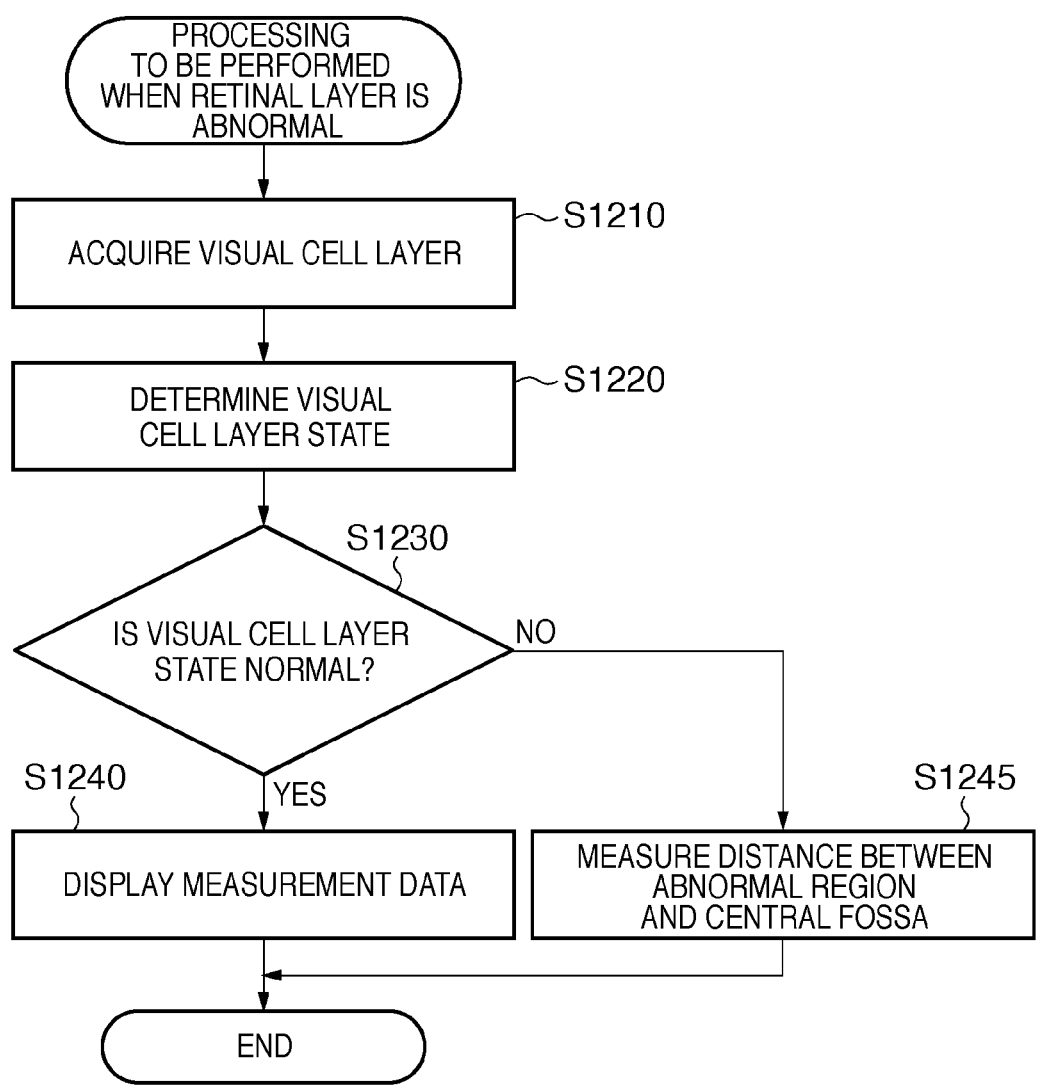
FIG. 12 is a flowchart showing the details of processing in step S465 according to the second embodiment of the present invention.

Step S465 is processing to be performed when a retinal layer thickness is abnormal. The details of the processing in this step will be described with reference to FIG. 12.

<Step S1210>

In step S1210, the layer acquisition unit 331 acquires a visual cell inner segment/outer segment boundary (not shown) and the upper boundary (not shown) of a pigmented retinal layer from a tomogram. For example, the layer acquisition unit 331 can acquire these boundaries by using luminance values or edge information in the A-scan direction (y direction).

<Step S1220>

In step S1220, the state determination unit 333 obtains the distance between the visual cell inner segment/outer segment boundary (not shown) and the upper boundary (not shown) of the pigmented retinal layer. If the obtained distance is smaller than the normal value of the visual cell layer acquired from the storage unit 320, the state determination unit 333 determines that the visual cell layer state is abnormal. The coordinates of the abnormal region and the distance from it are stored in the storage unit 320.

<Step S1230>

In step S1230, the changing unit 332 causes the process to branch in accordance with the determination result obtained in step S1220. That is, if it is determined that the visual cell layer state is normal, the changing unit 332 instructs the display unit 340 to perform processing (the process advances to step S1240). If it is determined that the visual cell layer state is abnormal, the changing unit 332 instructs the quantifying unit 336 to perform processing (the process advances to step S1245).

<Step S1240>

In step S1240, the display unit 340 superimposes and displays the result acquired in step S1210 and the tomogram.

<Step S1245>

In step S1245, the quantifying unit 336 acquires the coordinates of the abnormal region and the visual cell layer thickness from the storage unit 320, and measures the distance between the central fossa 1001 and the abnormal region in the x-axis direction. If the distance between the abnormal region and the central fossa is equal to or less than a threshold, the display unit 340 displays the position of the abnormal region and the layer thickness.

Executing the processing from step S1210 to step S1245 described above can implement the processing in step S465.

As described above, according to this embodiment, the image processing apparatus 900 can determine whether the retinal layer thickness of an eye to be examined is normal, and acquire diagnosis information data suitable for each case.

That is, in this embodiment, when the layer is abnormal, this apparatus measures the thickness of the visual cell layer (or the thickness from the visual cell inner segment/outer segment boundary to the pigmented retinal layer) as the diagnosis information data of the eye region. The apparatus then determines whether the thickness of the visual cell layer is normal. If the thickness is abnormal, the apparatus measures, as diagnosis information data of the eye region, the distance from the central fossa of a region in which the visual cell layer is thin.

[Third Embodiment]

The image processing apparatus 10 according to the first embodiment causes the state determination unit 333 to determine a layer state, and causes the changing unit 332 to determine an image processing algorithm in accordance with the determination result. The image processing apparatus according to third embodiment is the same as that according to the first embodiment in that it determines an image processing algorithm in accordance with the layer state determination result obtained by a state determination unit 333. Note, however, that the third embodiment differs from the first embodiment in that a changing unit 332 changes image processing parameters as image processing algorithms in accordance with the determination result obtained by the state determination unit 333.

In addition, the image processing apparatus according to this embodiment is the same as the image processing apparatus 900 according to the second embodiment, and the arrangement of the system is the same as that of the first embodiment.

In this embodiment, consider a case in which circular scanning is performed for an optic papilla to measure a nerve fiber layer thickness. Assume that the normal value range of nerve fiber layer thicknesses has been loaded from a data server 40 into a storage unit 320 in advance.

Specific processing performed by the image processing apparatus (image processing apparatus 900) according to this embodiment basically follows the flowchart shown in FIG. 4, but differs only in the following point.

<Step S430>

In step S430, a layer acquisition unit 331 detects an internal limiting membrane 3 and a nerve fiber layer boundary 4 from a tomogram.

<Step S440>

Figure 13:
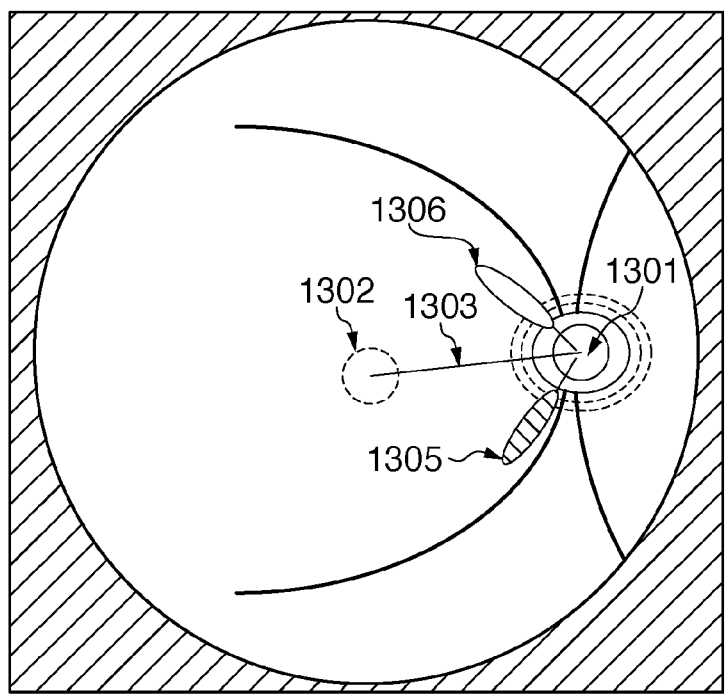
FIG. 13 is a view for explaining processing in step S440 according to the third embodiment of the present invention.

In step S440, the state determination unit 333 determines, based on the detection result obtained in step S430, whether the thickness of a nerve fiber layer 2 is normal. More specifically, first of all, the state determination unit 333 acquires the normal value range of nerve fiber layer thicknesses from the storage unit 320. In step S430, the state determination unit 333 determines, based on the internal limiting membrane 3 and the nerve fiber layer boundary 4 detected in step S430, whether the nerve fiber layer thickness falls within the normal value range. In this case, it is possible to perform this determination based on the layer thickness ratio or difference value at an area 1306 which is line-symmetric to an abnormal region 1305 shown in FIG. 13 (areas which are symmetric with respect to a line segment 1303 connecting an optic papilla 1301 and a macular region 1302). The storage unit 320 stores the determination result on the state of the nerve fiber layer 2 and, if there is a nerve fiber layer thickness abnormal region, the position, area, and thickness of the region.

<Step S450>

In step S450, the changing unit 332 causes the process to branch (i.e., change the algorithm) in accordance with the determination result obtained in step S440. That is, if it is determined that the nerve fiber layer thickness is normal, the changing unit 332 transmits a signal to instruct the quantifying unit 336 to execute processing (the process advances to step S460). If it is determined that the nerve fiber layer thickness is abnormal, the changing unit 332 changes image processing parameters in accordance with the position, area, and layer thickness of the abnormal region, and then transmits a signal to instruct the layer acquisition unit 331 to execute processing (the process advances to step S465).

<Step S460>

Step S460 is processing to be performed when the nerve fiber layer thickness is normal. The contents of the processing in this step is the same as that in step S520, and hence a description of this step will be omitted.

<Step S465>

Figure 14:
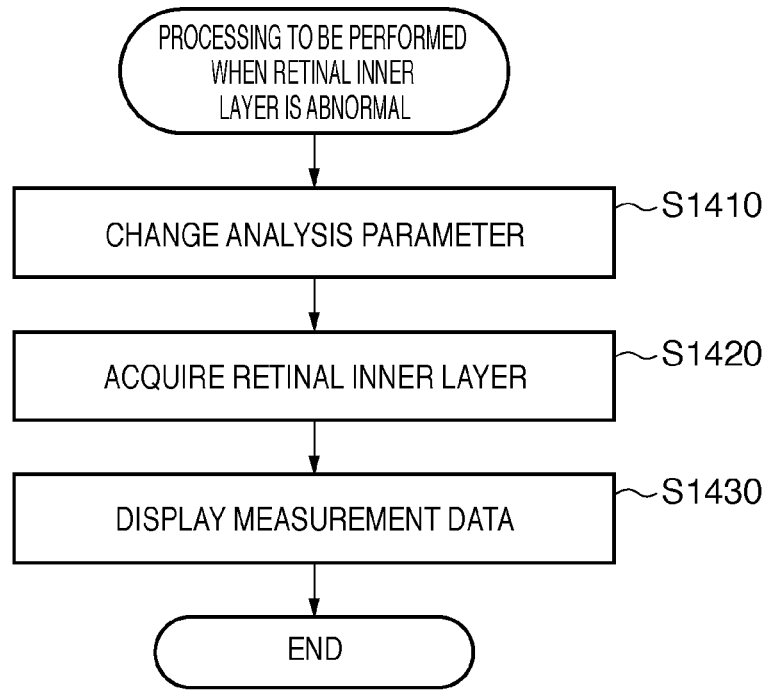
FIG. 14 is a flowchart showing the details of processing in step S465 according to the third embodiment of the present invention.

Step S465 is processing to be performed when the nerve fiber layer thickness is abnormal. The details of the processing in this step will be described with reference to FIG. 14.

<Step S1410>

In step S1410, the changing unit 332 acquires the coordinates, area, and layer thickness of the nerve fiber layer thickness abnormal region from the storage unit 320. As a method of changing image processing parameters (analysis parameters), for example, a spatial range in which image processing is performed and processing intervals are re-set in the following manner. That is, the image processing target area is enlarged to make the abnormal region be sufficiently included in the image processing target area (such that the abnormal region does not exist near the boundary of the image processing target area) within the range in which the target area does not exceed the imaging area of a tomogram of the eye region. In addition, if there is an abnormal region, short processing intervals are set to analyze an area including the abnormal region in detail.

<Step S1420>

In step S1420, the layer acquisition unit 331 re-measures the nerve fiber layer thickness by using the image processing parameters re-set in step S1410. If there is a nerve fiber layer thickness abnormal region, the coordinates, area, and layer thickness of the abnormal region are stored in the storage unit 320.

<Step S1430>

In step S1430, a display unit 340 superimposes the nerve fiber layer thickness acquisition result in step S1420 on the tomogram and displays the superimposed image.

Executing the processing in steps S1410 to S1430 in this manner will implement the processing in step S465 described above.

As described above, according to this embodiment, the image processing apparatus can determine whether the nerve fiber layer thickness of an eye to be examined is normal, and acquire diagnosis information data suitable for each case. That is, if the layer is abnormal, the apparatus changes image processing parameters such as the spatial range of image processing and processing intervals, direction, and sequence in accordance with the position and area of a portion of the nerve fiber layer in which the layer becomes thin, and measures diagnosis information data such as a nerve fiber layer thickness.

(First Modification)

The method of changing image processing parameters using the changing unit 332 is not limited to the above example. Consider, for example, a case in which the image processing apparatus further includes a fundus image acquisition unit which acquires a fundus image by using a fundus camera to obtain diagnosis information data of an eye region by using a fundus image and a tomogram. If the state determination unit 333 determines that there is a lesion at an end of a tomogram processing target area, the changing unit 332 can issue an instruction to change image processing parameters for a fundus image so as to make the lesion be included in the processing target area of the fundus image. Alternatively, this apparatus may be configured to process a fundus image upon making the changing unit 332 issue an instruction to change image processing parameters for the fundus image so as to decrease processing intervals near the lesion.

(Second Modification)

It is not always necessary to independently execute the respective methods of changing image processing algorithms using the changing unit 332, which have been described in the first to third embodiments. That is, it is possible to execute these methods in combination. For example, while layer state determination is performed a plurality of number of times as in the second embodiment, the changing unit 332 can issue an instruction to change image processing parameters in accordance with the state determination result as in the third embodiment. In addition, it is possible to execute the first and second embodiments in combination. Obviously, it is possible to execute any embodiments in combination.

[Other Embodiment]

The present invention can also be implemented by executing the following processing. That is, this is the processing of supplying software (programs) for implementing the functions of the above embodiments to a system or an apparatus via a network or various kinds of storage media, and causing the computer (or CPU, MPU, or the like) of the system or apparatus to read out and execute the programs.

The present invention is not limited to the above embodiments and various changes and modifications can be made within the spirit and scope of the present invention. Therefore, to apprise the public of the scope of the present invention, the following claims are made.

This application claims the benefit of Japanese Patent Application No. 2008-269186 filed on Oct. 17, 2008, which is hereby incorporated by reference herein in its entirety.

The invention claimed is:

1. An image processing apparatus which processes a tomogram of an eye region, the image processing apparatus comprising:
    a processor; and
    a memory storing instructions that, when executed by the processor, cause the image processing apparatus to:
        acquire a predetermined layer area from the tomogram;
        change an algorithm for acquiring, based on information extracted from the predetermined layer area, diagnosis information as information to be used for diagnosis of the eye region from the tomogram; and
        acquire the diagnosis information from the tomogram based on the changed algorithm.

2. The image processing apparatus according to claim 1, wherein the memory further stores instructions that, when executed by the processor, cause the image processing apparatus to acquire the tomogram.

3. The image processing apparatus according to claim 1, wherein the memory further stores instructions that, when executed by the processor, cause the image processing apparatus to:
  determine a state of the layer based on the acquired predetermined layer area; and
  change the algorithm in accordance with the determined state of the layer.

4. The image processing apparatus according to claim 3, wherein the memory further stores instructions that, when executed by the processor, cause the image processing apparatus to determine whether a state of the predetermined layer area is normal.

5. The image processing apparatus according to claim 3, wherein the memory further stores instructions that, when executed by the processor, cause the image processing apparatus to:
  acquire a second layer area as information for acquiring the diagnosis information from the tomogram,
  wherein the instructions that cause the image processing apparatus to change the algorithm for acquiring diagnosis information include instructions that cause the image processing apparatus to determine, in accordance with the determined state of the layer, whether to acquire the second layer area.

6. The image processing apparatus according to claim 3, wherein the memory further stores instructions that, when executed by the processor, cause the image processing apparatus to estimate a normal structure of the layer on the tomogram as information for acquiring the diagnosis information, wherein the instructions that cause the image processing apparatus to change the algorithm for acquiring diagnosis information include instructions that cause the image processing apparatus to determine to execute estimation of a normal structure, when it is determined that the state of the layer is not normal.

7. The image processing apparatus according to claim 6, wherein the memory further stores instructions that, when executed by the processor, cause the image processing apparatus to quantify a state of the layer by using one of a thickness distribution, area, volume, density feature indicated by a difference between the predetermined layer area and an estimated normal structure of the layer.

8. The image processing apparatus according to claim 3, wherein the instructions that cause the image processing apparatus to change the algorithm for acquiring diagnosis information includes instructions that cause the image processing apparatus to change a target area for image processing for acquisition of the diagnosis information, a direction of processing, a processing sequence, and processing intervals based on a position, area or volume, and shape of an abnormal region of the layer, when it is determined that the state of the layer is not normal.

9. The image processing apparatus according to claim 3, wherein the predetermined layer is at least one of layers existing in a range from an internal limiting membrane to an inner plexiform layer, and
  wherein the memory further stores instructions that, when executed by the processor, cause the image processing apparatus to determine whether a state of the layer is normal by using at least one piece of information of a detected layer thickness and an index indicating an indentation shape or statistics thereof.

10. The image processing apparatus according to claim 3, wherein the predetermined layer is at least one of layers existing in a range from an external limiting membrane to a pigmented retinal layer, and
  wherein the memory further stores instructions that, when executed by the processor, cause the image processing apparatus to determine whether the state of the layer is normal by using at least one piece of information of information indicating a presence/absence of the layer and a detected layer thickness and statistics concerning an extreme value of a point sequence constituting the detected layer, the number of inflection points, a curvature, and an angle.

11. The image processing apparatus according to claim 3, wherein the predetermined layer is an overall retinal layer, and
  wherein the memory further stores instructions that, when executed by the processor, cause the image processing apparatus to determine whether the state of the layer is normal by using information indicating a presence/absence of the layer and a detected layer thickness.

12. The image processing apparatus according to claim 1, wherein the memory further stores instructions that, when executed by the processor, cause the image processing apparatus to quantify a state of the layer by using one of a shape and layer thickness of the predetermined layer area.

13. The image processing apparatus according to claim 1, wherein the memory further stores instructions that, when executed by the processor, cause the image processing apparatus to:
  externally acquire an instruction to store or not to store an acquired predetermined layer area; and
  output the acquired predetermined layer area when an instruction to store is acquired.

14. The image processing apparatus according to claim 1, wherein the predetermined layer is at least one of layers existing in a range from an internal limiting membrane to an inner plexiform layer.

15. The image processing apparatus according to claim 1, wherein the predetermined layer is at least one of layers existing in a range from an external limiting membrane to a pigmented retinal layer.

16. The image processing apparatus according to claim 1, wherein the predetermined layer is an overall retinal layer.

17. An image processing method performed by an image processing apparatus which processes a tomogram of an eye region, the image processing method comprising:
  acquiring a predetermined layer area from the tomogram;
  changing an algorithm for acquiring, based on information extracted from the layer area, diagnosis information as information to be used for diagnosis of the eye region from the tomogram; and
  acquiring the diagnosis information from the tomogram based on the changed algorithm.

18. A non-transitory computer-readable storage medium which stores a computer program that, when executed by a computer, causes an image processing apparatus, which processes a tomogram of an eye region, to perform an image processing method comprising:
  acquiring a predetermined layer area from the tomogram;
  changing an algorithm for acquiring, based on information extracted from the predetermined layer area, diagnosis information as information to be used for diagnosis of the eye region from the tomogram; and
  acquiring the diagnosis information from the tomogram based on the changed algorithm.

* * * * *